(12) United States Patent
Peter et al.

(10) Patent No.: US 8,221,530 B2
(45) Date of Patent: Jul. 17, 2012

(54) WATER TRAP

(75) Inventors: Gerd Peter, Lübeck (DE); Thomas Maxeiner, Lübeck (DE); Thomas Wuske, Bad Malente (DE)

(73) Assignee: Draeger Medical GmbH, Luebeck (DE)

(*) Notice: Subject to any disclaimer, the term of this patent is extended or adjusted under 35 U.S.C. 154(b) by 250 days.

(21) Appl. No.: 12/801,369

(22) Filed: Jun. 4, 2010

(65) Prior Publication Data
US 2010/0307341 A1   Dec. 9, 2010

(30) Foreign Application Priority Data
Jun. 5, 2009   (DE) .......................... 10 2009 024 040

(51) Int. Cl.
*B01D 53/22* (2006.01)
(52) U.S. Cl. ................. 96/9; 95/43; 95/45; 95/52; 96/4; 96/7
(58) Field of Classification Search ................ 95/43, 45, 95/52; 96/4, 7, 9
See application file for complete search history.

(56) References Cited

U.S. PATENT DOCUMENTS

| | | | | |
|---|---|---|---|---|
| 3,416,985 A * | 12/1968 | Dounoucos | .................. | 156/289 |
| 3,976,451 A * | 8/1976 | Blackmer et al. | .................. | 96/7 |
| 4,853,013 A * | 8/1989 | Rio et al. | ............. | 96/6 |
| 4,924,860 A | 5/1990 | Larsen et al. | | |
| 5,800,597 A * | 9/1998 | Perrotta et al. | ...................... | 96/9 |
| 6,030,436 A * | 2/2000 | Barclay | ............................. | 95/45 |
| 6,117,214 A | 9/2000 | Peter et al. | | |
| 6,309,448 B1 * | 10/2001 | Mizobe | ............................ | 96/7 |
| 7,402,197 B2 | 7/2008 | Larsen et al. | | |
| 2009/0084383 A1 | 4/2009 | Maxeiner et al. | | |

* cited by examiner

*Primary Examiner* — Jason M Greene
*Assistant Examiner* — Anthony Shumate
(74) *Attorney, Agent, or Firm* — Walter Ottesen

(57) ABSTRACT

A water trap (1) improved with respect to handling and operational safety includes: two semipermeable membranes (2) and at least one tank (7), wherein the membranes have a water penetration pressure greater than 750 hPa and are made of the same or different PTFE laminates. The gas flow is divided in a ratio between 10:90 and 25:75 into the flush-/purge branch and analysis branch to the sensors (12) and a path parallel to the sensors (12), respectively, with the aid of the membranes and downstream filter elements and via the material and configuration.

16 Claims, 2 Drawing Sheets

WATER TRAP

CROSS REFERENCE TO RELATED APPLICATION

This application claims priority of German patent application no. 10 2009 024 040.3, filed Jun. 5, 2009, the entire contents of which is incorporated herein by reference.

FIELD OF THE INVENTION

The invention relates to a water trap with two semipermeable membranes and at least one tank.

BACKGROUND OF THE INVENTION

Such water traps are disclosed, for example, in U.S. Pat. No. 6,117,214 and United States patent application publication 2009/0084383.

In water traps used hitherto for anesthetic gases or for anaesthetic devices for measuring the respiratory gas of a patient drawn off by suction, either exclusively gas permeable and liquid impermeable PTFE-(Polytetrafluoroethylene)-membranes are used or filter elements are used in addition to a PTFE-membrane. The filter elements are intended to noticeably increase their gas flow resistance when coming in contact with water and to prevent water from penetrating.

Disadvantageous in the water traps of the first type without an additional filter element is that foreign substances, which are transported along with the sample gas stream, collect on the surface of the PTFE-membrane over time during the course of operation. These foreign substances reduce the hydrophobic effect of the PTFE-membranes and eventually lead to a wetting of the PTFE-membranes and to a through passage of liquids or condensate.

In water traps of the second type (for example, water traps of the Criticare Company), it is disadvantageous that the additional filter elements cause a significant pressure drop already in the dry state because of their structure. The pressure range available for taking patient gas measurements is thereby noticeably limited.

If, in the case of a fault, water passes through the membrane and reaches the filter elements, the pressure drop across these elements increases noticeably as a result of the fine pored structure. Nonetheless, the danger persists that liquids pass through these filter elements at corresponding pressure conditions, especially at pressure differentials of greater than 500 hPa.

SUMMARY OF THE INVENTION

There is therefore a need for a water trap in which the product attributes have been improved and which fulfills the following requirements.

With the filter elements used there should be little or no change in their gas flow resistance as a result of the effect of specimen gas flow suctioned from the patient's mouthpiece. When contacted by water or aqueous liquids, the filter elements should permanently seal and not allow any further specimen gas flow from the patient to the gas measuring apparatus, so that an inflow of liquids and the damage associated therewith to the connected gas measurement sensors can be prevented. A contact between the filter elements and liquids should be indicated by a change of color so that the condition of these filter elements ("wet"-"dry") can easily be determined by a user. The filter elements additionally arranged in the water trap must not have a negative influence on the system response time of the connected gas measurement sensors, for instance, by a blurring of the measurement signals resulting from an abrupt change in gas concentration. The filter elements should be bio-compatible if possible, so that the specimen gas flowing through the filter elements can subsequently be returned to the breathing loop/patient.

The water trap of the invention includes: an inlet for receiving a gas flow; two semipermeable membranes having a water penetration pressure greater than 750 hPA and being comprised of PTFE laminates; a tank; two filter elements arranged downstream of corresponding ones of the semipermeable membranes; a sensor; a first one of the semipermeable membranes and a first one of the filter elements defining a first path communicating with the inlet and forming a gas analysis path to the sensor; a second one of the semipermeable membranes and a second one of the filter elements defining a second path communicating with the inlet and a flush/purge path parallel to the first path and the sensor; and, the semipermeable membranes and the filter elements being configured to direct the gas flow via the first and second paths at a ratio lying in a range of 90/10 to 75/25.

The solution to the above problem is achieved through the use of filter elements made of a plastic sinter body to which a superabsorber polymer (SAP) and a colorant indicator have been admixed. A (polyethylene) PE-granulate was sintered, which has a particle size between 300 and 400 μm (XM-1213, Porex Company) and to which an SAP-granulate was added with a particle size of less than 300 μm (Luquasorb 1030, BTC/BASF) and a proportion between 10% and 20%, preferably 15%. The SAP-addition only moderately absorbs moisture in its gaseous state and thereby maximally changes the gas flow resistance of the filter elements by a factor of 3 (at room temperature and 100% humidity).

The resulting gas flow resistance when using a specimen gas flow of 200 ml/min rises from 2 to about 4 hPa in dry conditions to maximally 12 hPa during operation with a moist measuring gas.

When water impinges upon the filter element, the resistance increases abruptly and the filter element seals itself hermetically, so that even if water acts for over 24 hours with a water column higher than 8 m, corresponding to a pressure differential of over 800 hPa, no water can pass through. Damage to the connected gas sensors because of penetrated aqueous liquids is thereby effectively prevented.

Additionally, a preferably water soluble colorant was added with about 0.1% by weight. This colorant is finely distributed in the filter element in small colorant pigments and is invisible as long as the filter element does not get wet. Only when contacted by water or aqueous solutions does the colorant dissolve and color the filter element so as to be clearly visible.

In the case where a patient is ventilated with large inspiratory—expiratory airway pressure differentials (Pdiff=Paw−Ppeep), it has been shown to be disadvantageous in known water traps that artefacts appear in the gas concentration courses depending on the amount of the pressure differential Pdiff at the moment of switching from the inspiratory to the expiratory phase. These artefacts are especially visible on the $CO_2$-concentration course, that is, in a capnogram.

These artefacts develop as a result of the patient gas stored in the tank with the captured liquid with a composition of the patient gas resulting as a time average over several inspiration and expiration phases. During the inspiratory phase, which is characterized by an increased airway pressure, the gas pressure in the tank rises correspondingly. At the time of the switch to the expiratory phase having a lower respiratory pressure, the gas expands out of the tank and reaches the analysis branch. This leads to a temporary disturbance in the measurement values over time for the determined gas concentrations. The magnitude of these artefacts scale to the airway pressure differential and the tank volume.

According to an additional aspect of the water trap, an additional antechamber is integrated therein and is arranged between the tank and the drainage opening of the analysis membrane. The volume of this chamber was selected so that it amounts to about 1/100 of the volume of the tank at an antechamber volume of about 0.15 ml and a tank volume of about 15 ml. If the above described pressure compensation processes occur, it can now be effectively prevented that the gas from the tank directly reaches the analysis branch. Instead, for the most part, only the gas stored in the antechamber reaches the analysis branch. In this case, disturbances of the concentration courses are prevented, since the gas concentration in the antechamber always corresponds well to the gas concentration in the analysis branch.

An additional advantage of the water trap of the invention over previous water traps with housings of highly transparent plastics such as polycarbonates (PC) or PMMA (polymethyl methacrylate) lies in the improved readability of the fill level of the usually clear condensate/water, which had been hardly possible previously.

The improved readability is achieved in that the tank is assembled from or consists of a clear front part (Polypropylene, PP) and a dark, particularly dark blue colored, rear part which preferably also consists of polypropylene. Furthermore, the inside of the front part of the tank is provided with a surface structure (roughened) so that, when light shines on the empty tank from the front, which corresponds to the typical operating conditions, it leads to an increased backscatter of the incoming light and thereby leads to a white-like bright visual impression. Here, the structuring can preferably be implemented as a roughening or in prism-like structures with a refractive angle of 45°. The backscattering of the incoming light takes place due to the structured plastic surfaces, which are at an angle to the direction of the incoming light, because of partial total reflection and is dependent on the jump of the refractive index at the boundary surface: plastic material (PP, $n_{pp} \cong 1.5$) to Air ($n_{Air} \cong 1$). If the tank is now partially filled with condensate/water, then the jump of the refractive index at this boundary surface decreases ($n_{water} \cong 1.33$) and thereby the proportion of backscattered light decreases. Since no light can pass directly out of the dark colored rear part of the tank or through the light-tight holder, the fill height is clearly shown via a light-dark contrast between the filled (dark) and empty (light) parts of the tank.

A further advantage of the present water trap compared to previous water traps is set forth in the following.

If a previous water trap is full or partially full and is held horizontally, the condensate collected in the tank can reach the opening closed by a purge membrane. Because of adhesion forces between the plastic (PP) used and the condensate or water, a water lens forms in front of this opening, so that the membrane has a gas-proof seal and, as a result of the gas flow direction, it remains closed during operation. The consequence of the water lens is the clogging of the water trap when condensate is in the incoming gas flow, since no more drainage of condensate occurs into the tank because drainage is only ensured by the gas flow via the purge membrane.

To additionally solve this known problem of known water traps, a perpendicular channel structure is arranged below the purge-membrane opening and a part is provided which surrounds this opening and this part leads the water in a funnel-like fashion into the channel. The mode of operation of such an arrangement is characterized in that, at the same time as the water lens is formed, the channel structure is filled with water, for instance, when the water trap is completely filled with water and then, during emptying of the water trap, the water runs downwardly through the channel because of the force of gravity. The water in the water lens is also pulled into the channel because of the acting cohesion forces thereby clearing the opening again.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
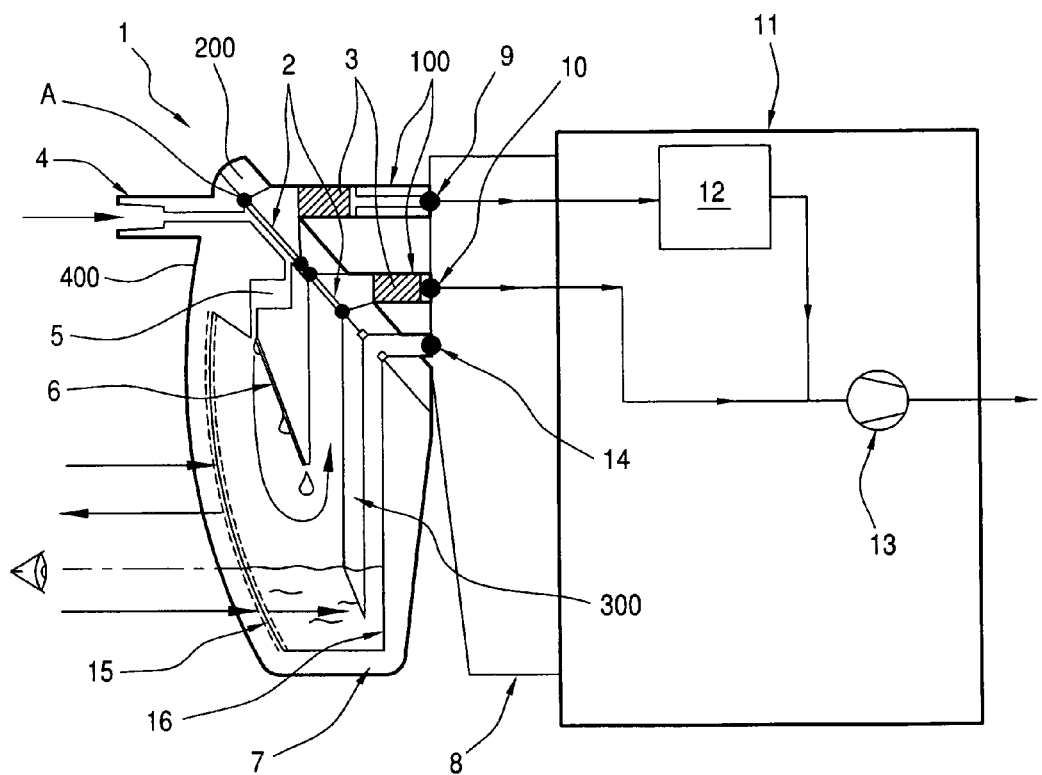
FIG. 1 is a section view of the water trap on a holder with a connected gas measuring module.

The water trap 1 in FIG. 1 is releasably attached to the holder 8. The holder 8 is connected downstream to the gas measuring module 11 via three ports, that is, connections, namely an analysis port 9, a purge port 10 and a service port 14. The gas measuring module 11 has one or more gas sensors 12 to measure the respiratory gas to be analyzed as well as a pump 13 for moving the measurement gas or gas being measured. The gas sensors 12 are, for example, infrared optical sensors to determine the concentration of selected respiratory gas components. The measurement gas flows from an aspiration location (not shown) in a patient-respiratory gas line via the measurement gas inlet 4 into the water trap 1. Via two semipermeable PTFE-membranes 2, the measurement gas is separated from moisture contained therein with the liquid being captured in the tank 7.

An intermediate piece 200 is disposed between housing member 400 and the holder 8. As shown in FIG. 1, the two semipermeable membranes are surrounded by respective elastomer rings A. The plastic housing parts, namely, housing part 400 and intermediate piece 200, are configured to enclose the membranes 2. These housing parts are joined to each other at a joint connection by a joining process so as to cause the joint connection to generate the needed compression of the elastomer rings A to ensure gas tightness and water tightness. The joint connection can be made with a plastic laser-welding process.

The water trap 1 has an antechamber 5 to minimize respiratory path pressure-induced artefacts.

A run-off edge 6, for example, having a width of 0.7 mm and a length of 12.5 mm ensures that the water transported into the tank 7 runs off on the rear side of the tank 7 (shown to the right in FIG. 1) without spraying the front side of the tank (shown to the left in FIG. 1). The front side 15 of the tank 7 is manufactured out of a transparent material such as polypropylene. The rear part 16 is colored dark, preferably dark blue, so that, because of a structured surface of the front side 15, a fill-height dependent backscatter of incoming light results which improves the readability of the fill height.

The filter elements 3 comprise plastic sintered bodies, to which a super absorbent polymer (SAP) and a colorant indicator were added. Here, a (polyethylene)PE-granulate was sintered which has a particle size between 300 and 400 μm (XM-1213, Porex Technologies GmbH), and to which was admixed a SAP-granulate having a particle size of <300 μm (Luquasorb 1030, BTC/BASF) in a proportion between 10% and 20%, preferably 15%. The SAP addition absorbs moisture in its gaseous state only Moderately and thereby changes the gas flow resistance of the filter elements 3 by at most a factor of 3 (at room temperature and 100% humidity).

The resulting gas flow resistance with a sample gas flow of 200 ml/min thereby increases from 2 to about 4 hPa in the dry state to a maximum of 12 hPa during operation with moist measurement gas.

If water impinges on a filter element 3, then the resistance increases abruptly and the filter element 3 seals itself hermetically, so that even if there is contact for more than 24 hours and a water column greater than 8 m, corresponding to a pressure differential of over 800 hPa, no water can pass through. Damage to the connected gas sensors 12 caused by water-containing liquid can hereby be effectively prevented. Additionally, a preferably water-soluble colorant is added of about 0.1% by weight. This colorant is finely distributed in the filter elements 3 in small colorant pigments and is invisible so long as the filter element or elements have not become wet. The colorant only dissolves and thereby clearly noticeably colors the filter element 3 when contacted by water or an aqueous solution.

Figure 3:
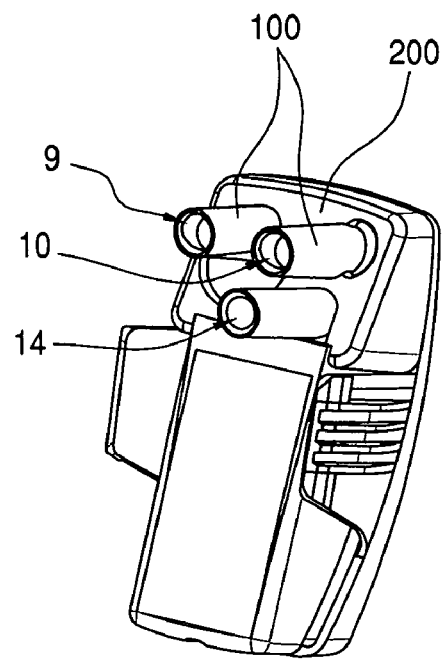

The intermediate piece 200 disposed between housing member 400 and holder 8 includes connectors 100 for accommodating corresponding ones of the filter elements 3. FIG. 3 is a perspective view of the intermediate piece 200 showing the arrangement of the connectors 100.

Figure 2:
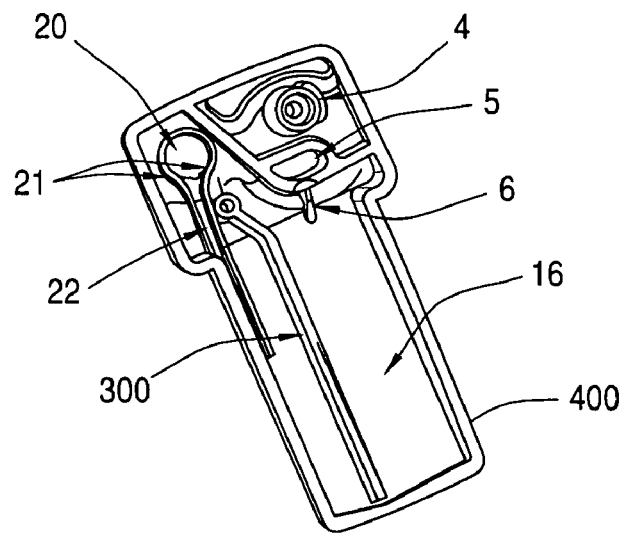
FIG. 2 is a detailed view of a housing part of the water trap according to FIG. 1; and, FIG. 3 is a perspective view of an intermediate piece having connectors for accommodating filter elements therein.

FIG. 2 schematically shows the configuration of a device to remove a water lens which forms in front of the purge membrane 20. The device has a channel 22 or channel structure as well as a part which guides the water in a funnel-like manner into the channel 22 via a funnel structure 21.

The purge membrane 20 is one of the two membranes 2 of FIG. 1 and is arranged upstream of the purge port 10.

The gas-tight channel 300 shown in FIG. 2 communicates with the service port 14. As shown in FIG. 1, the gas-tight channel 300 is integrated into the water trap so as to extend to the bottom of the tank 7.

The service port 14 is adapted to accommodate a syringe having a Luerlock connector so as to permit emptying the water trap via the gas-tight channel 300.

It is understood that the foregoing description is that of the preferred embodiments of the invention and that various changes and modifications may be made thereto without departing from the spirit and scope of the invention as defined in the appended claims.

What is claimed is:

1. A water trap comprising:
   an inlet for receiving a gas flow;
   two semipermeable membranes having a water penetration pressure greater than 750 hPA and being comprised of PTFE laminates;
   a tank;
   two filter elements arranged downstream of corresponding ones of said semipermeable membranes;
   a sensor;
   a first one of said semipermeable membranes and a first one of said filter elements defining a first path communicating with said inlet and forming a gas analysis path to said sensor;
   a second one of said semipermeable membranes and a second one of said filter elements defining a second path communicating with said inlet and a flush/purge path parallel to said first path and said sensor; and,
   said semipermeable membranes and said filter elements being configured to direct said gas flow via said first and second paths at a ratio lying in a range of 90/10 to 75/25.

2. The water trap of claim 1, further comprising:
   two elastomeric rings configured to surround corresponding ones of said semipermeable membranes;
   plastic housing parts configured to enclose said membranes; and,
   said housing parts being joined to each other at a joint connection by a joining process so as to cause said joint connection to generate the needed compression of said elastomeric rings to ensure gas tightness and water tightness.

3. The water trap of claim 2, wherein said joint connection is made with a plastic laser-welding process.

4. The water trap of claim 1, wherein said membranes are surrounded by an adhesive edge to ensure water tightness; and, said water trap further comprising a laser-welded intermediate part for holding said filter element to ensure a needed gas tightness to the ambient.

5. The water trap of claim 2, wherein said first and second filter elements are self-sealing filter elements which seal in response to contact with water while simultaneously displaying a color change; and,
   said first and second filter elements are each comprised of:
   a sintered PE-granulate having particle sizes of 300 to 400 μm and said sintered PE-granulate having a superabsorber additive of 10 to 20% by weight.

6. The water trap of claim 5, wherein each of said first and second filter elements further comprises a water-soluble colorant additive.

7. The water trap of claim 6, wherein said water-soluble colorant additive is a food colorant additive.

8. The water trap of claim 7, wherein said food colorant additive is approximately 0.1% by weight.

9. The water trap of claim 5, wherein said first path includes an analysis port arranged downstream of said first filter and a purge port arranged downstream of said second filter; first and second connectors corresponding to said analysis port and said purge port, respectively.

10. The water trap of claim 9, wherein said first and second connectors each have an inner diameter of approximately 4.7 mm and are at an axial spacing of approximately 13 mm.

11. The water trap of claim 2, further comprising a device for removing a water lens which forms in front of the second one of said semipermeable membranes; and, said device comprising a channel and a funnel-shaped structure for guiding the water of said water lens to said channel.

12. The water trap of claim 1, further comprising an antechamber upstream from the tank and said antechamber being configured to minimize airway pressure induced artefacts.

13. The water trap of claim 1, wherein said tank has a front wall having a structured surface and a rear wall; said front wall is comprised of a substantially transparent material and said rear wall is colored, so that said structured surface causes a fill-level dependent backscatter of incident light thereby improving the readability of the fill level.

14. The water trap of claim 13, wherein said transparent material is polypropylene.

15. The water trap of claim 1, further comprising a service port; a gas-tight channel connected directly to said service port and being integrated into said water trap so as to extend to the bottom of said tank; and, said service port being adapted to accommodate a syringe having a Luerlock connector so as to permit emptying said water trap via said gas-tight channel.

16. The water trap of claim 1, further comprising an edge-like structure formed from the same material as the remaining housing and configured to direct water transported into said tank to the rear of said tank without spraying on the front side of said tank.

* * * * *